(12) United States Patent
Miyasaka et al.

(10) Patent No.: US 9,907,799 B2
(45) Date of Patent: Mar. 6, 2018

(54) TAU AGGREGATION INHIBITOR

(71) Applicants: THE DOSHISHA, Kyoto (JP); National Center for Geriatrics and Gerontology, Aichi (JP)

(72) Inventors: Tomohiro Miyasaka, Kyoto (JP); Hachiro Sugimoto, Kyoto (JP); Rie Tokizane, Hyogo (JP); Yuki Shinzaki, Kyoto (JP); Yohei Oe, Kyoto (JP); Tetsuo Ota, Kyoto (JP); Akihiko Takashima, Saitama (JP); Yoshiyuki Soeda, Fukushima (JP); Yasuo Ihara, Kyoto (JP); Yoshikazu Inoue, Kyoto (JP)

(73) Assignees: THE DOSHISHA, Kyoto (JP); National Center for Geriatrics and Gerontology, Aichi (JP)

( * ) Notice: Subject to any disclaimer, the term of this patent is extended or adjusted under 35 U.S.C. 154(b) by 0 days.

(21) Appl. No.: 14/781,897

(22) PCT Filed: Apr. 2, 2014

(86) PCT No.: PCT/JP2014/001919
§ 371 (c)(1),
(2) Date: Oct. 1, 2015

(87) PCT Pub. No.: WO2014/162737
PCT Pub. Date: Oct. 9, 2014

(65) Prior Publication Data
US 2016/0030437 A1    Feb. 4, 2016

(30) Foreign Application Priority Data

Apr. 2, 2013 (JP) .................................. 2013-076614

(51) Int. Cl.
| | | |
|---|---|---|
| *A61K 31/5375* | (2006.01) |
| *A61K 31/05* | (2006.01) |
| *A61K 31/055* | (2006.01) |
| *A61K 31/11* | (2006.01) |
| *A61K 31/12* | (2006.01) |
| *A61K 31/136* | (2006.01) |
| *A61K 31/085* | (2006.01) |
| *A61K 31/137* | (2006.01) |

(52) U.S. Cl.
CPC .......... *A61K 31/5375* (2013.01); *A61K 31/05* (2013.01); *A61K 31/055* (2013.01); *A61K 31/085* (2013.01); *A61K 31/11* (2013.01); *A61K 31/12* (2013.01); *A61K 31/136* (2013.01); *A61K 31/137* (2013.01)

(58) Field of Classification Search
CPC .................................................... A61K 31/535
USPC ................................................... 514/238.8
See application file for complete search history.

(56) References Cited

U.S. PATENT DOCUMENTS

| | | |
|---|---|---|
| 3,671,625 A | 6/1972 | Altounyan |
| 4,690,949 A | 9/1987 | Yoshida et al. |
| 2001/0047032 A1 | 11/2001 | Castillo et al. |
| 2002/0161002 A1 | 10/2002 | Epstein et al. |
| 2003/0060487 A1 | 3/2003 | Bamdad et al. |
| 2004/0152760 A1 | 8/2004 | Castillo et al. |
| 2005/0009925 A1 | 1/2005 | Bymaster et al. |
| 2005/0107472 A1 | 5/2005 | Wischik et al. |
| 2007/0191330 A1 | 8/2007 | Castillo et al. |
| 2010/0167286 A1 | 7/2010 | Reijo Pera et al. |
| 2011/0065657 A1 | 3/2011 | Castillo et al. |
| 2011/0136832 A1 | 6/2011 | Herz et al. |
| 2011/0144124 A1* | 6/2011 | Snow ................... C07C 231/02 514/255.01 |
| 2012/0052053 A1 | 3/2012 | Manning-Bog et al. |
| 2014/0249180 A1 | 9/2014 | Takashima et al. |
| 2015/0044193 A1 | 2/2015 | Manning-Bog et al. |

FOREIGN PATENT DOCUMENTS

| | | |
|---|---|---|
| EP | 2 764 863 A1 | 8/2014 |
| JP | 2003-532634 A | 11/2003 |
| JP | 2004-534854 A | 11/2004 |
| JP | 2012-508740 | 4/2012 |
| JP | 2003-530432 | 10/2013 |
| WO | 01/78709 A2 | 10/2001 |
| WO | 03/020257 A2 | 3/2003 |
| WO | 2008/121412 A1 | 10/2008 |
| WO | 2009003147 | 12/2008 |

(Continued)

OTHER PUBLICATIONS

Daccache, A. et al, "Oleuropein and derivatives from olives as Tau aggregation inhibitors," Neurochemistry International, 2011, vol. 58, No. 6, pp. 700-707.
Crowe, A. et al, "Identification of Aminothienopyridazine Inhibitors of Tau Assembly by Quantitative High-Throughput Screening," Biochemistry, 2009, vol. 48, No. 32, pp. 7732-7745.
International Search Report dated Jun. 24, 2014 for PCT/JP2014/001919.
International Search Report dated Apr. 4, 2013 for PCT/JP2012/006363.
Wolozin, Benjamin et al., "Olfactory Neuroblasts from Alzheimer Donors: Studies on APP Processing and Cell Regulation," Biol Psychiatry 34 (1993) 824-838.

(Continued)

*Primary Examiner* — Yong Chu
(74) *Attorney, Agent, or Firm* — Knobbe Martens Olson & Bear LLP

(57) ABSTRACT

A tau aggregation inhibitor can sufficiently inhibit a tau protein from aggregating in cells. The inhibitor includes a 4-substituted catechol structure compound, having, at position 4 of its catechol ring, an electron-donating substituent R other than a hydrocarbon group, or a salt thereof. The 4-substituted catechol structure compound is preferably 4-aminocatechol or 1,2,4-benzenetriol. Examples of tauopathies to which this inhibitor is applicable include AD, Down's syndrome, frontotemporal dementia, cotricobasal degeneration (CBD) and progressive supranuclear palsy (PSP).

2 Claims, 10 Drawing Sheets

(56) References Cited

FOREIGN PATENT DOCUMENTS

| WO | WO-2009003147 | * | 12/2008 |
|---|---|---|---|
| WO | 2011/071920 A2 | | 6/2011 |
| WO | 2013/051266 A1 | | 4/2013 |

OTHER PUBLICATIONS

Wang, Wenfei et al., "Compounds blocking mutant huntingtin toxicity identified using a Huntington's disease neuronal cell model," Neurobiology of Disease 20 (2005) 500-508.
Iqbal, Khalid et al., "Tau in Alzheimer Disease and Related Tauopathies," Curr Alzheimer Res. 7(8) (2010) 656-664.
Partial European Search Report dated Apr. 10, 2015 for EP Application 12837822.1.
Meek, A. et al., "In silico search for an endogenous anti-Alzheimer's molecule — Screening amino acid metabolic pathways", Can. J. Chem., 2012, vol. 90, pp. 865-873.
Ambree et al., "Levodapa ameliorates learning and memory deficits in a murine model of Alzheimer's disease," Neurobioloty of Aging 30 (2009) 1192-1204.
Li et al., "Dopamine and L-dopa disaggregate amyloid fibrils: implications for Parkinson's and Alzheimer's disease," The FASEB Journal 18 (2004) 962-964.
Houng et al., "Catechol derivatives inhibit the fibril formation of amyloid-β peptides," Journal of Bioscience and Bioengineering 109:6 (2010), 629-634.
Ono et al., "Anti-Parkinsonian agents have anti-amyloidogenic activity for Alzheimer's β-amyloid fibrils in vitro," Neurochemistry International 48 (2006) 275-285.
Aiken et al., "A cell-based screen for drugs to treat Huntington's disease," Neurobiology of Disease 16 (2004) 546-555.
Konkar et al., "β-Adrenoceptor Subtype Activities of Trimetoquinol Derivatives: Biochemical Studies of Human β-Adrenoceptors Expressed in Chinese Hamster Ovary Cells," The Journal of Pharmacology and Experimental Therapeutics 291 (1999) 875-883.
Pinder et al., "Hexoprenaline: A Review of its Pharmacological Properties and Therapeutic Efficacy with particular Reference to Asthma," Drugs 14 (1977) 1-28.
Extended European Search Report dated Oct. 15, 2015 for EP 12837822.1.
U.S. Appl. No. 14/349,160, filed Apr. 2, 2014, including its prosecution history, the references and the Office Actions therein.
Shimizu et al. "L-threo-3,4-dihydroxyphenylserine Treatment for Dementia of Various Etiologies," Proc. Japan Acad., 62, Ser. B (1986), pp. 205-208.
Partial Supplementary European Search Report dated May 3, 2016 for EP14779014.1.
Neary et al., "Frontotemporal lobar degeneration: A consensus on clinical diagnostic criteria," Neurology 1998:51:1546-1554.
U.S. Office Action dated Oct. 12, 2016, in U.S. Appl. No. 14/349,160, filed Apr. 2, 2014.
"About Dementia," © 2016 Alzheimer's Foundation of America, Page Last Updated Jan. 28, 2016, Retrieved from: http://www.alzfdn.org/AboutDementia/symptoms.html.
J. G. Cannon Chapter Nineteen in Burger's Medicinal Chemistry and Drug Discovery, Fifth Edition, vol. 1: Principles and Practice, Wiley-Interscience 1995, pp. 783-802, 784.
Venkatesan. "What is the difference between dopamine and dobutamine and what is the clinical significance," Mar. 25, 2009, https://drsvenkatesan.com/2009/03/25/what-is-the-difference-between-dopamine-and-dobutamine-and-what-is-the-clinical-significance/, printed Mar. 27, 2017, 2 pages.
Office Action dated Mar. 31, 2017 for U.S. Appl. No. 14/349,160, filed Apr. 2, 2014, 19 pages.
Office Action dated Sep. 13, 2017 for U.S. Appl. No. 14/349,160, filed Apr. 2, 2014, 13 pages.

* cited by examiner

TAU AGGREGATION INHIBITOR

CROSS REFERENCE TO RELATED APPLICATIONS

This application is the U.S. National Phase of International Application No. PCT/JP2014/001919, Apr. 2, 2014, designating the U.S. and published in Japanese as WO 2014/162737A1 on Oct. 9, 2014 which claims the benefit of Japanese Patent Application No. 2013-076614, filed Apr. 2, 2013. Any and all applications for which a foreign or domestic priority claim is identified here or in the Application Data Sheet as filed with the present application are hereby incorporated by reference under 37 CFR 1.57.

TECHNICAL FIELD

The present invention relates to a tau aggregation inhibitor for inhibiting the formation of a tau aggregate which would cause a neurologic deficit and synapse elimination.

BACKGROUND ART

Alzheimer's disease (AD) is a kind of dementia, of which the major symptoms include a cognitive decline and a personality change. Dementia is a common disease by which approximately 25% of Japanese elderly people of age 85 or older are affected, and AD accounts for about 50% of all kinds of dementia. As of 2011, Japan has approximately 1.6-1.8 million AD patients, the number of which should go on rising as the elderly people account for an increasing percentage of the world population in the future. This is a particularly serious problem for Japan, in which the number of children per household has been falling while the number of elderly people has been rising recently.

An acetylcholinesterase inhibitor, which is believed to be most effective in preventing and treating AD, is in fact only partially effective for patients with a mild or moderate degree of disease, and its effectiveness for patients with an advanced degree of disease is denied by a lot of people.

Although AD is actually characterized by senile plaque of β amyloid and by Neurofibrillary Tangles (NFT) formed by abnormal tau protein polymerization, recent neuropathological comments about AD patients indicate that the current mainstream AD research is based on an amyloid β hypothesis that an abnormal amyloid β peptide triggers the AD symptom.

However, it has recently been found that in the familial frontotemporal dementia (FTDP), the dementia symptom expresses itself due the formation of NFTs promoted by the mutation of a tau gene, and abnormality is caused in nerve cells just by aggregation and accumulation of the tau protein in the brain. Thus, people have recently been paying a lot of attention to the correlation between the tau aggregation and the onset of AD.

The tau protein is a kind of protein which is present in profusion in central nerve cells and which is indispensable for the neuroaxis that forms a neural network in the brain to function properly. However, once the tau protein formed an insoluble aggregate in cells, the axonal transport would no longer work fine to cause the death of nerve cells.

Patent Document 1 discloses a drug which includes, as its main ingredient, a naphtho quinone compound that inhibits the tau aggregation in order to alleviate the symptom of AD. With this drug, the tau aggregation in cells is reduced to a certain extent, and therefore, the formation of NFTs is suppressed to the point that the symptom of AD is alleviated.

CITATION LIST

Patent Document

PATENT DOCUMENT 1: Japanese Unexamined Patent Application Publication (Translation of PCT Application) No. 2004-534854

SUMMARY OF INVENTION

The tau aggregation inhibitor described above, however, cannot sufficiently inhibit the tau aggregation in cells, and cannot be regarded as contributing to treating various tauopathies such as AD properly.

In view of the foregoing background, it is therefore an object of the present invention to provide a tau aggregation inhibitor which can sufficiently inhibit the tau aggregation in cells.

A tau aggregation inhibitor according to an embodiment includes: catechol; and a 4-substituted catechol structure compound having, at position 4 of its catechol ring, an electron-donating substituent R other than a hydrocarbon group; or a 3-substituted catechol structure compound having, at position 3 of its catechol ring, an electron-donating substituent R; or a salt of any of these compounds.

A tau aggregation inhibitor according to another embodiment includes a catechol structure compound selected from the group consisting of 2,3-dihydroxybenzaldehyde, 4-tert-butylcatechol, 3,4-dihydroxybenzylamine, 4-chloroacetyl catechol, 1-(3,4-dihydroxyphenyl)-2-morpholino ethanol, and 4-chlorocatechol, and salts thereof.

According to the present invention, the tau aggregation is sufficiently suppressed in cells, thus allowing for remedying patients with AD and other tauopathies, against which there have been no effective cures so far, and eventually making a lot of contributions to the forthcoming aging society by improving the living standards of the elderly, lightening the burden of long-term care, and cutting down the medical expenses.

BRIEF DESCRIPTION OF THE DRAWINGS

FIG. 8 shows the thioflavin T activities of various kinds of compounds, wherein.

FIG. 10 shows the thioflavin T activities of various kinds of compounds, wherein.

FIG. 12 shows the thioflavin T activities of various kinds of compounds, wherein.

FIG. 13 shows the results of electrophoresis carried out on sarcosyl soluble tau and sarcosyl insoluble tau, wherein

DESCRIPTION OF EMBODIMENTS

Figure 1:
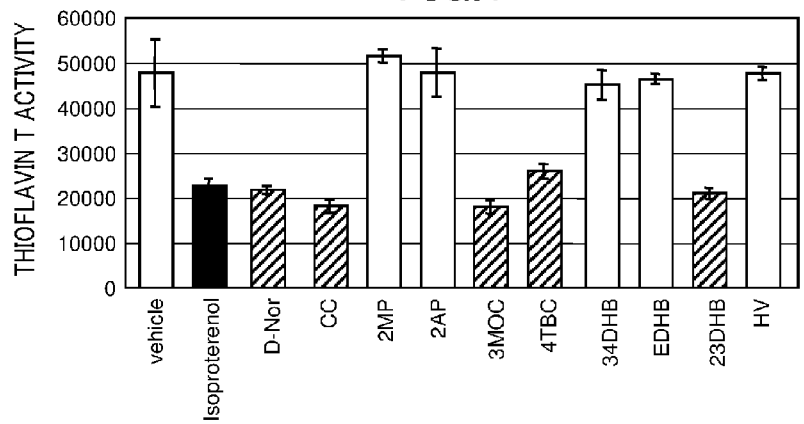
FIG. 1 shows the thioflavin T activities of eleven different kinds of compounds.

Embodiments of the present invention will now be described in detail with reference to the accompanying drawings. Note that those embodiments will be described just for the sake of allowing the reader to understand more easily the principle of the present invention and that the scope of the present invention is not limited to the following description of embodiments. Rather, various other embodiments that would be readily created by those skilled in the art by appropriately modifying the configuration of the embodiment to be described below also fall within the scope of the present invention.

As a result of intensive researches, the present inventors newly discovered that a compound including: catechol; and a 4-substituted catechol structure compound having, at position 4 of its catechol ring, an electron-donating substituent R other than a hydrocarbon group; or a 3-substituted catechol structure compound having, at position 3 of its catechol ring, an electron-donating substituent R would work effectively in preventing and treating a tauopathy. Based on this finding, the present inventors perfected our invention.

In this description, the "catechol structure compound" refers herein to a compound having a catechol structure in its structural formula. The "catechol structure" refers herein to the structure of a catechol that is a compound in which two of the substituents of its benzene ring are hydroxyl groups that are located at ortho positions.

Also, the "electron-donating substituent R other than a hydrocarbon group" is obtained herein by excluding a hydrocarbon group from all substituents and by further selecting an electron-donating substituent. Examples of the "hydrocarbon groups" include an alkyl group, a group derived from alkene, and an aromatic hydrocarbon group.

The alkyl group is not limited to any particular group, but is preferably one of C1 to C6 alkyl groups with one to six carbon atoms. The C1 to C6 alkyl group may be a straight chain alkyl group or a branched chain alkyl group, for example. More specific examples of C1 to C6 alkyl groups include a methyl group, an ethyl group, an n-propyl group, an isopropyl group, an n-butyl group, an isobutyl group, a tert-butyl group, a sec-butyl group, an n-pentyl group, a neopentyl group, an n-hexyl group, an isohexyl group, and a 3-methylpentyl group. Those alkyl groups may include an alkyl group derivative such as an aminoalkyl group.

The group derived from alkene is not limited to any particular group, but may be $CH_2=CH-$, $CH_2=CHCH_2-$, or $CH_3CH=CH-$, for example. The aromatic hydrocarbon group (aryl group) is not limited to any particular group, but may be $C_6H_5$-phenyl group, $CH_3C_6H_4$-tolyl group (including o-, m- and p-), $(CH_3)_2C_6H_3$-xylyl group and $C_{10}H_7$-naphthyl group, for example.

The "electron-donating substituent R" is not limited to any particular substituent, but may be an electron-donating substituent selected from the group consisting of an amino group, a hydroxyl group, an alkoxy group, and a thiol group.

The amino group is $-NRR'$. R and R' indicate independently a hydrogen atom, an alkyl group, a cycloalkyl group, an aryl group, an aralkyl group or a heterocyclic group.

The alkyl group as R, R' is preferably a straight chain or branched chain alkyl group with a carbon number of one to six, and is more preferably a straight chain or branched chain alkyl group with a carbon number of one to five. The aralkyl group as R, R' is preferably an aralkyl group with a carbon number of seven to eleven, and may be a benzyl group, a phenyl ethyl group, a phenyl propyl group, a phenyl butyl group, or a naphthyl methyl group, for example. Optionally, one or more of the carbon atoms that form the alkyl chain of the alkyl and aralkyl groups may be replaced with an unsaturated bond, an ether bond or an ester bond, and R and R' may be bonded together to form a ring.

The cycloalkyl group as R, R' is preferably a cycloalkyl group with a carbon number of three to eight, and is more preferably a cycloalkyl group with a carbon number of three to six.

The aryl group as R, R' may be a phenyl group, a naphthyl group, an anthracenyl group, a triphenylenyl group, a pyrenyl group, or a fluorenyl group, for example.

The heterocyclic group as R, R' may be a five- to seven-membered aromatic heterocyclic ring, saturated heterocyclic ring, or unsaturated heterocyclic ring including not only carbon atoms but also one to four hetero atoms selected from the group consisting of nitrogen, oxygen and sulfur atoms, or a condensed heterocyclic ring in which these heterocyclic rings and a benzene ring are condensed together. Examples of preferred heterocyclic groups include a 2-furyl group, a 3-furyl group, a 2-thienyl group, a 3-thienyl group, a 2-oxazolyl group, a 2-oxazolinyl group, a 3-isooxazolyl group, a 4-isooxazolyl group, a 5-isooxazolyl group, a 3-isooxazolinyl group, a 2-thiazolyl group, a 2-thiazolinyl group, a 3-isothiazolyl group, a 3-isothiazolinyl group, a 2-pyranyl group, a 4-tetrahydropyranyl group, a 1-azetidinyl group, a 2-azetidinyl group, a 3-azetidinyl group, a 2-pyrrolyl group, a 2-pyrrolidinyl group, a 2-imidazolyl group, a 3-pyrrazolyl group, a 2-imidazolinyl group, a 2-pyrridyl group, a 3-pyrridyl group, a 4-pyrridyl group, a 2-piperidyl group, a piperidino group, a 2-morpholinyl group, a morpholino group, a 2-piperazinyl group, a 2-pyrimidinyl group, a 3-pyridazinyl group, and a 2-pyrazinyl group.

Optionally, the alkyl group, cycloalkyl group, aryl group, aralkyl group, or heterocyclic group may be replaced with at least one group selected from the group consisting of an amino group, a carboxy group, a hydroxyl group, a phenyl group, an alkoxy group, a sulfhydryl group, a carbonyl group, an aldehyde group, and a halogen group.

The alkoxy group refers herein to a group in which an alkyl group R is directly bonded to an oxygen atom (O). Examples of the alkyl groups indicated by R include a methyl group, an ethyl group, an n-propyl group, an isopropyl group, an n-butyl group, an isobutyl group, a sec-butyl group, a tert-butyl group, pentyl groups, hexyl groups, octyl groups, decyl groups, a cyclopentyl group, and a cyclohexyl group. The alkoxy group refers herein to a straight chain or branched chain alkoxy group such as methoxy, ethoxy, n-propoxy, isopropoxy, n-butoxy, isobutoxy, sec-butoxy, tert-butoxy, pentyloxy, hexyloxy, heptyloxy and octyloxy.

The 4-substituted catechol structure compound preferably has, at position 4 of its catechol ring, a substituent R which is any one of an amino group, a hydroxyl group, an alkoxy group and thiol group.

The 4-substituted catechol structure compound is particularly preferably either 4-aminocatechol or 1,2,4-benzenetriol.

Alternatively, the 4-substituted catechol structure compound may also be 4-(isopentylamino) catechol or 4-methoxycatechol.

Still alternatively, the 4-substituted catechol structure compound may also be 4-(4-aminobutanoylamino) catechol, 4-(morpholinocarbonylamino) catechol, or 4-(diisopentylamino) catechol.

The 3-substituted catechol structure compound preferably has, at position 3 of its catechol ring, a substituent R which is any one of an amino group, a hydroxyl group, an alkoxy group and thiol group.

The 3-substituted catechol structure compound is particularly preferably 3-methoxycatechol, pyrogallol, or 3-aminocatechol.

Another tau aggregation inhibitor may be selected from the group consisting of 2,3-dihydroxybenzaldehyde, 4-tert-butylcatechol, 3,4-dihydroxybenzylamine, 4-chloroacetylcatechol, 1-(3,4-dihydroxyphenyl)-2-morpholinoethanol, and 4-chlorocatechol. Still another tau aggregation inhibitor corresponds to an optical isomer other than 2S and 3R of 2-amino-3-(3,4-dihydroxyphenyl)-3-hydroxy propionate (droxidopa), for example. Compared to droxidopa, an optical isomer other than 2S and 3R of 2-amino-3-(3,4-dihydroxyphenyl)-3-hydroxy propionate would cause a lower metabolic elimination rate in vivo due to a difference in the conformation of the position 2-amino group, and therefore, would result in higher brain retention and higher in vivo stability. Such an isomer has a lower capacity, and can function for a longer time, than droxidopa. In addition, thanks to a difference in the conformation of the hydroxyl group located at position 3, such an isomer could reduce significantly binding to an adrenaline receptor in vivo, and consequently reduce significantly the side effects via the adrenaline receptor. The present invention is a tau polymerization inhibitor and its intended use is a long-term administration to the elderly. By using such an optical isomer appropriately, a higher degree of safety, a smaller dosage, and a smaller number of times of administration are achieved than when droxidopa is used. As a result, high superiority would be achieved in the treatment of dementia.

Yet another tau aggregation inhibitor corresponds to four kinds of optical isomers of 3-(3,4-dihydroxyphenyl)-3-hydroxy-2-(isopropylamino)propionate. Compared to droxidopa, the four kinds of optical isomers of 3-(3,4-dihydroxyphenyl)-3-hydroxy-2-(isopropylamino)propionate would be able to reduce the side effects in an organism via an α adrenaline receptor, because the amino group has been turned into isopropyl in these optical isomers. In addition, since metabolic elimination advances at a higher rate in these optical isomers than in droxidopa, the drug can be removed quickly, even when some side effects are produced. Considering the intended use of the tau polymerization inhibitor of the present invention is long-term administration to the elderly, such optical isomers are readily used for treatment highly safely, and would be superior to droxidopa.

A tau aggregation inhibitor according to this embodiment may use any of these catechol structure compounds either by itself or in combination.

A tau aggregation inhibitor according to this embodiment further includes their salts, which are pharmacologically acceptable salts. Examples of those salts include: alkali metal salts (such as potassium salts and sodium salts), alkaline earth metal salts (such as magnesium salts and calcium salts) and other metal salts; alkali carbonate metals (such as lithium carbonate, potassium carbonate, sodium carbonate, and cesium carbonate), alkali hydrogen carbonate metals (such as lithium hydrogen carbonate, sodium hydrogen carbonate, and potassium hydrogen carbonate), alkali metal hydroxides (such as sodium hydroxide and potassium hydroxide) and other salts of inorganic bases; trialkylamine (such as trimethylamine and triethylamine), pyridine, quinoline, piperidine, imidazole, picoline, dimethylaminopyridine, dimethylaniline, N-alkyl-morpholine, DBN, DBU and other salts of organic bases; hydrochlorides, hydrobromides, hydroiodides, sulfates, nitrates, phosphates and other salts of inorganic acids; formates, acetates, propionates, oxalates, malonates, succinates, fumarates, maleates, lactates, malates, citrates, tartrates, carbonates, picrates, methanesulfonates, glutamates and other salts of organic acids.

Optionally, a tau aggregation inhibitor according to this embodiment may share its effective dose with a pharmaceutically acceptable carrier. As the carrier, a solid such as an excipient or a liquid such as a diluent may be used. Examples of specific carriers include magnesium stearate, lactose, starch, gelatin, agar, talc, pectin, acacia, olive oil, sesame oil, cacao butter, ethylene glycol, and distilled water.

The "tauopathy" refers herein to a neurodegenerative disease characterized in that accumulation of phosphorylated tau is seen in nerve cells and glial cells. Examples of the tauopathies include AD, Down's syndrome, frontotemporal dementia, cotricobasal degeneration (CBD) and progressive supranuclear palsy (PSP).

In this description, "to prevent a tauopathy" means herein preventing a tauopathy disorder from occurring, and "to treat a tauopathy" means herein either preventing a tauopathy disorder from advancing, or alleviating or relieving the tauopathy disorder.

A tau aggregation inhibitor according to this embodiment may include, as appropriate, one or more additives selected from the group consisting of a tonicity agent, a buffer agent, a solubilizing agent, an antiseptic agent, and a pH adjusting agent that are pharmaceutically acceptable.

Examples of the tonicity agents include potassium chloride, sodium chloride, boric acid, mannitol, glycerin, propylene glycol, polyethylene glycol, maltose, sucrose, sorbitol, and glucose.

Examples of the buffer agents include organic acids such as amino acid and succinic acid, inorganic acids such as boric acid and phosphoric acid, and other medicinally acceptable salts.

Examples of the solubilizing agents include: polyethylene glycol, polyvinyl pyrrolidone, polyvinyl alcohol, hydroxypropylmethyl cellulose and other polymers; polysorbate, polyoxyethylene hydrogenated castor oil, polyoxyethylene, polyoxypropylene and other surfactants; propylene glycol and other polyhydric alcohols; benzoic acid, sorbic acid and other organic acids; aspartic acid, histidine, glycine, lysine and other amino acids.

Examples of the antiseptic agents include: benzethonium, benzalkonium, benzododecinium and other quaternary ammonium salts; chlorhexidine and other salts of cationic compounds; methyl parahydroxybenzoate, propyl parahydroxybenzoate and other parahydroxybenzoate esters; and chlorobutanol, benzyl alcohol and other alcohol compounds.

Examples of the pH adjusting agents include sulfuric acid, hydrochloric acid, acetic acid, lactic acid, calcium hydroxide, potassium hydroxide, sodium hydroxide, magnesium hydroxide, monoethanol amine, triethanol amine, diisopropanol amine, and triisopropanol amine.

The dosage of a tau aggregation inhibitor according to this embodiment is not particularly limited as long as intended effects are produced, and is determined appropriately with the degree of symptom, sex, age and other factors of the patient, to which the inhibitor is going to be administered, taken into consideration. The dosage of the tau aggregation inhibitor administered to an adult person per day may be in the range of 0.0001 to 1000 mg, for example. This dosage per day may be administered at a time in one day but may also be divided into a few dosages to be separately administered multiple times in one day.

A tau aggregation inhibitor according to this embodiment may be prepared into any appropriate form of medicine according to the mode of administration. The medicine may be administered orally in a solid form such as granule, pill, tablet, capsule, or powder, or in a liquid form. On the other hand, the medicine may also be administered non-orally by injection such as intravenous or intramuscular injection.

When phosphorylated, tau molecules are associated with each other to form a tau oligomer. As this tau oligomer grows to have a β sheet structure, a spherical granular tau aggregate is formed. The granular tau aggregate would be comprised of approximately 40 tau molecules. These granular tau aggregates are combined together to form a tau fiber called "paired helical filament (PHF)" through NFTs. A recent study using a mouse model revealed that if the overexpression of tau was suppressed at a timing when NFTs were formed, the mice's memory learning skills improved, but NFTs continued being formed. This result suggests that a decline in nerve function was not caused by NFTs themselves but had rather been caused while those NFTs were being formed. The NFTs themselves would not have toxicity, but the neurotoxicity would have been caused mostly by the aggregation process to form the NFTs. A tau aggregation inhibitor according to this embodiment inhibits the tau aggregation not only during a process in which the PHF is formed by allowing the granular tau aggregates to combine with each other but also during a process in which spherical granular tau aggregates are formed. The nerve cells of the brain are denatured due to not only accumulation of mutated tau protein but also accumulation of normal tau protein as well. A tau aggregation inhibitor according to the present invention also inhibits the aggregation of the normal tau protein, and therefore, may be used to prevent or treat AD and any other tauopathy symptoms.

EXAMPLES

First of all, a plasmid expressing human-type tau 0N4R isoform (383 amino acid) was introduced into *E. coli* BL21 (DE3) strain to purify a recombinant tau. The purification was carried out by modifying the method of Taniguchi et al. (see Taniguchi et al., 2008, JBC, 280, 7614). A soluble fraction was prepared based on *E. coli* in which tau expression had been induced with isopropyl-β-thiogalactopyranoside, and then fractionation was carried out with a phosphocellulose column (e.g., P11 column produced by Whatman). The fraction eluted at an NaCl concentration of 0.1 to 0.3 M was recovered to perform precipitation and concentration using ammonium sulfate. The precipitate thus obtained was dissolved in a buffer containing 0.5 M of NaCl and 2% of 2-mercaptoethanol and then heated to 100° C. for five minutes. Then, the reactant was subjected to a centrifugation at 15,000×g for 15 minutes. The supernatant thus obtained was recovered and then subjected to precipitation and concentration with ammonium sulfate. The precipitate thus obtained was dissolved in a solution containing 20% of acetonitrile and 0.1% of formic acid so as to be purified using reversed phase HPLC (with a Cosmosil protein-R column produced by Nacalai Tesque). Fractions including full-length recombinant tau were mixed together and then the mixture thus obtained was dried with a freeze dryer to obtain a dried and purified recombinant tau sample. The yield and concentration of the tau thus obtained were analyzed by Coomassie Brilliant Blue (CBB) staining after the product was subjected to electrophoresis using 10% polyacrylamide gel.

The dried and purified recombinant tau sample was dissolved in purified water at a concentration of 0.9 mg/ml. Then, this solution was diluted so that thioflavin T with a final concentration of 10 μM, 0.1 M NaCl, 0.45 mg/ml recombinant tau, 10 mM HEPES pH7.4 and various compounds would have target concentrations. Next, their fluorescence value (under excitation light at 360 nm and fluorescent light at 465 nm) was measured with a fluorescent plate reader (infinit F200 produced by TECAN). Thereafter, heparin was added so that the concentration would be 60 μg/ml and then incubation was carried out at 37° C. in a moisture retention box to measure a variation in fluorescence value with time. The incubation was carried out for 168 hours, the fluorescence value was measured, and then the reacted solution was recovered to prepare a sarcosyl insoluble fraction. The sarcosyl insoluble fraction was made to have a final concentration of 1% by adding an aqueous solution of 10% (one-tenth quantity of) sodium N-lauroyl-sarcosinate to the reacted solution recovered. The solution was subjected to incubation at 4° C. for 30 minutes and then subjected to a centrifugation at 100,000×g for 20 minutes to separate the supernatant and the precipitate from each other. With the supernatant fraction and the precipitate regarded as a soluble tau fraction and a sarcosyl insoluble fraction, respectively, the yield of tau was analyzed by electrophoresis using 10% polyacrylamide gel. Also, part of the reacted solution was fractionated by sucrose density-gradient centrifugation using the method of Maeda et al. (see Maeda et al., 2007, Biochemistry, 46, 3856). After the centrifugation, the reactant was fractioned into 1 to 6 according to density and the tau yield was analyzed by 10% polyacrylamide gel electrophoresis and Western blotting.

As for structural development, the tau aggregation inhibition experiment described above was carried out by either purchasing or synthesizing a compound in which the structure of isoproterenol was divided into the four parts of: (A) two hydroxyl groups with a catechol skeleton; (B) a benzene ring with the catechol skeleton; (C) an α-hydroxyl group; and (D) an isopropylamide group and their structures were partially modified. During screening, the concentration of the compound was supposed to be 1 μM and compared to the effect achieved by 1 μM of isoproterenol under the same incubation condition.

Figure 2:
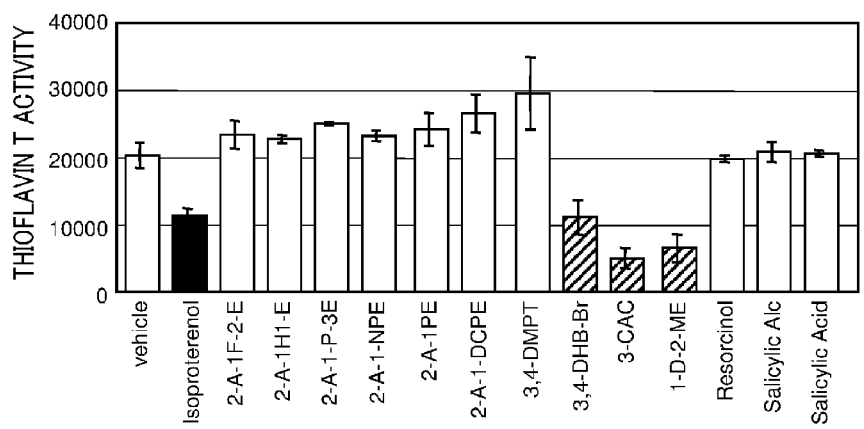
FIG. 2 shows the thioflavin T activities of fourteen different kinds of compounds.

First of all, to verify the effect achieved by the catechol skeleton itself, the structure-activity correlation of (A) was studied. FIGS. 1 and 2 show the respective thioflavin T activities of various kinds of compounds. As shown in FIGS. 1 and 2, catechol (indicated by CC and represented by the following Chemical Formula (1)) is a compound having as high tau polymerization inhibitory activity as isoproterenol, but no effects were produced by any of 2-methoxyphenol (indicated by 2-MP and represented by the following Chemical Formula (2)), 2-aminophenol (indicated by 2-AP and represented by the following Chemical Formula (3)), resorcinol (represented by the following Chemical Formula (4)), salicylic alcohol (represented by the following Chemical Formula (5)), and salicylic acid (represented by the following Chemical Formula (6)), each of which had been obtained by transforming any hydroxyl group.

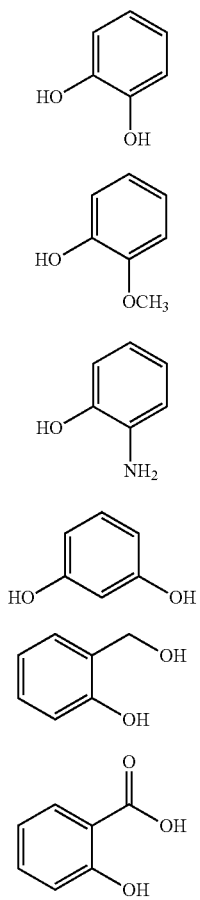

Also, as shown in FIGS. 1 and 2, (S)-(+)-Norepinephrine (D-Nor) and thioflavin T activities were compared to each other with respect to various kinds of compounds. No tau polymerization inhibitory activities were achieved by 2-amino-1-phenylethanol (indicated by 2-A-1PE and represented by the following Chemical Formula (7)) or 2-amino-1-(3,4-dichlorophenyl)ethanol (indicated by 2-A-1-DCPE and represented by the following Chemical Formula (8)). Neither homoveratylamine (indicated by HV and represented by the following Chemical Formula (9)) nor 2-(3,4-dimethoxy)ethylamine (indicated by 3,4-DMPT and represented by the following Chemical Formula (10)) exhibited any tau polymerization inhibitory activity.

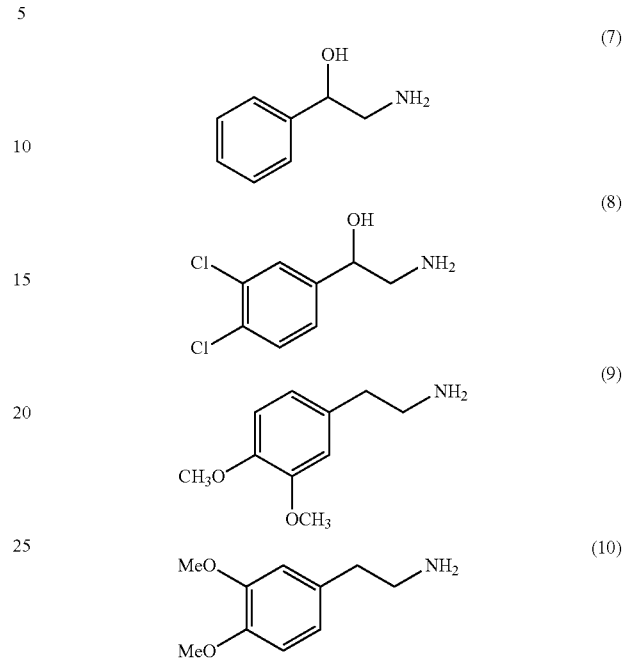

Figure 3:
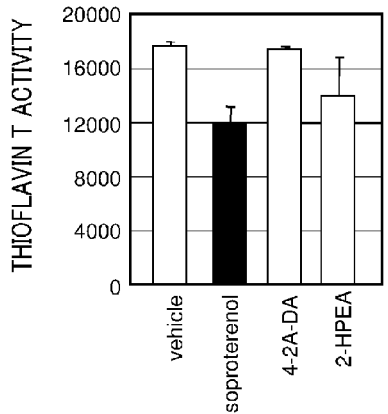
FIG. 3 shows the thioflavin T activities of three different kinds of compounds.

Next, the present inventors tried to change the catechol nucleus itself. The present inventors studied the tau polymerization inhibitory activities of the following compounds, of which the catechol nuclei were replaced with a furan ring, 1-methylimidazole ring, a pyridine ring, a nitrophenyl ring, a chlorophenyl ring, an aminophenyl ring, a dimethylphenyl ring, and a hydroxyphenyl ring, respectively: namely, 2-amino-1-(furan-2-yl)ethanol (indicated by 2-A-1F-2-E and represented by the following Chemical Formula (11)), 2-amino-1-(1-methyl-1H-imidazol-2-yl)ethanol (indicated by 2-A-1H1-E and represented by the following Chemical Formula (12)), 2-amino-1-(pyridine-3-yl)ethanol (indicated by 2-A-1-P-3E and represented by the following Chemical Formula (13)), 2-amino-1-(4-nitrophenyl)ethanol (indicated by 2-A-1-NPE and represented by the following Chemical Formula (14)), 1-(3,4-dimethylphenyl)ethylamine (indicated by 34DMPT and represented by the following Chemical Formula (15)), and 1-(2-hydroxyphenyl)ethylamine (indicated by 2-HPEA and represented by the following Chemical Formula (16)). FIG. 3 shows the thioflavin T activities of various kinds of compounds. As shown in FIGS. 2 and 3, none of these compounds exhibited the tau polymerization inhibitory activity.

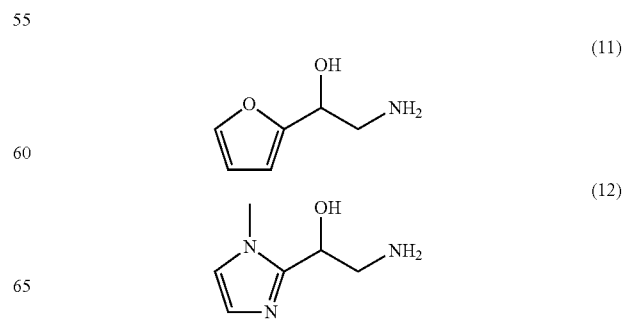

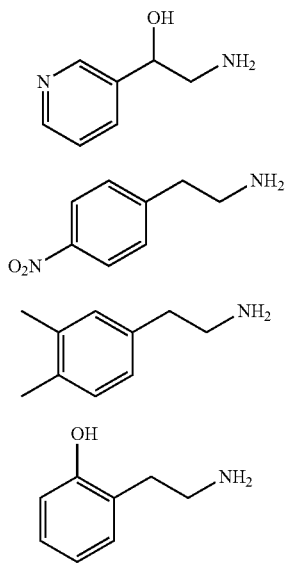

(13)

(14)

(15)

(16)

Taking these results into consideration, the present inventors regarded the catechol skeleton and two adjacent phenolic hydroxyl groups as indispensable ones to achieve the tau polymerization inhibitory activity.

Figure 4:
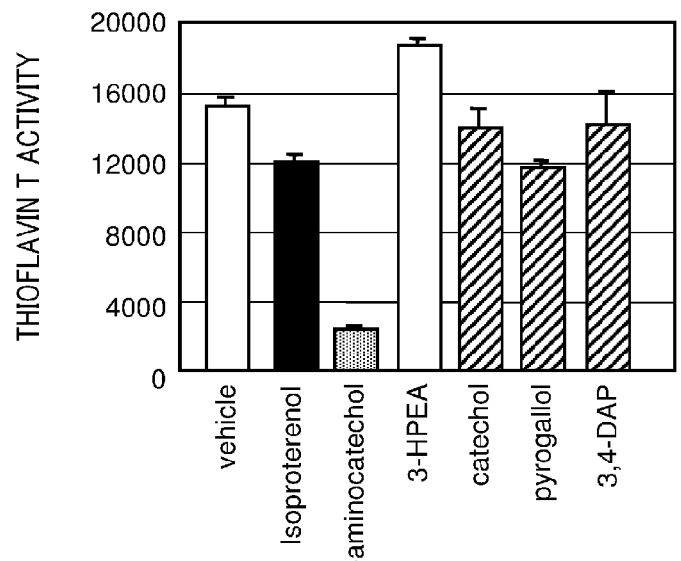
FIG. 4 shows the thioflavin T activities of six different kinds of compounds.
Figure 5:
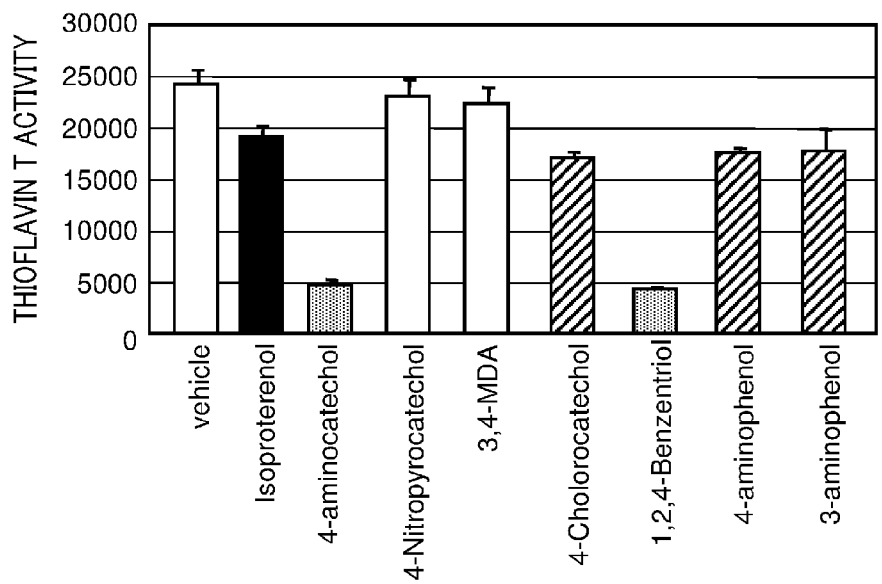
FIG. 5 shows the thioflavin T activities of eight different kinds of compounds.

Next, the present inventors studied the influence of the substituent located at position 4 of the catechol nucleus. In isoproterenol, the substituent is 2-isopropylamino-1-hydroxyethyl group, which was replaced with an aminomethyl group, a tert-butyl group, a chloro group, and a ketone group. That is to say, the present inventors examined the tau polymerization inhibitory activities of 3,4-dihydroxybenzylamine (represented by the following Chemical Formula (17)), 4-tert-butylcatechol (indicated by 4TBC and represented by the following Chemical Formula (18)), 4-chlorocatechol (represented by the following Chemical Formula (19)), and 3,4-dihydroxyacetophenone (indicated by 34-DAP and represented by the following Chemical Formula (20)). FIGS. 4 and 5 show the thioflavin T activities of various kinds of compounds. As shown in FIG. 1, 2, 4, 5, these compounds exhibited as high tau polymerization inhibitory activity as isoproterenol and catechol.

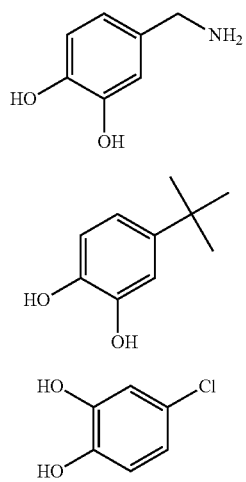

(17)

(18)

(19)

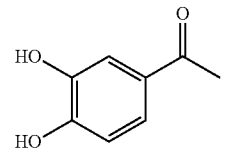

(20)

Also, as shown in FIG. 1, the present inventors confirmed that 3-methoxycatechol (indicated by 3MOC and represented by the following Chemical Formula (21)) and 2,3-dihydroxybenzaldehyde (indicated by 23 MB and represented by the following Chemical Formula (22)) also exhibited as high tau polymerization inhibitory activity.

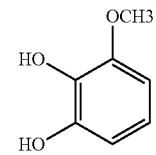

(21)

(22)

On the other hand, as shown in FIG. 1, the present inventors discovered that 3,4-dihydroxybenzaldehyde (indicated by 34 DHB and represented by the following Chemical Formula (23)) and ethyl 3,4-dihydroxybenzoic acid (indicated by EDHB and represented by the following Chemical Formula (24)), of which the substituent at position 4 was replaced with an aldehyde group and an ethoxycarbonyl group, respectively, exhibited no tau polymerization inhibitory activity.

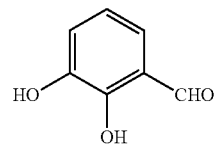

(23)

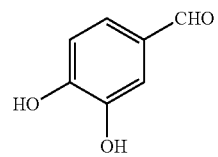

(24)

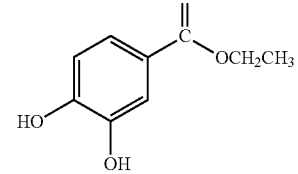

On the other hand, as shown in FIG. 2, 4-chloroacetylcatechol (indicated by 4-CAC and represented by the following Chemical Formula (25)) and 1-(3,4-dihydroxyphenyl)-2-morpholinoethanol (indicated by 1-D-2-ME and represented by the following Chemical Formula (26)) exhibited somewhat higher tau polymerization inhibitory activity than isoproterenol and catechol.

(25)
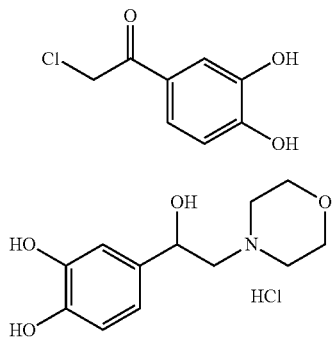

(26)

Based on the results of these experiments, the present inventors discovered that a compound, of which the substituent for position 4 of catechol was a carbon chain, exhibited as high tau polymerization inhibitory activity as isoproterenol and catechol did and that the effects diminished when the substituent was aldehyde, carboxylic acid or a nitro group, for example.

Figure 6:
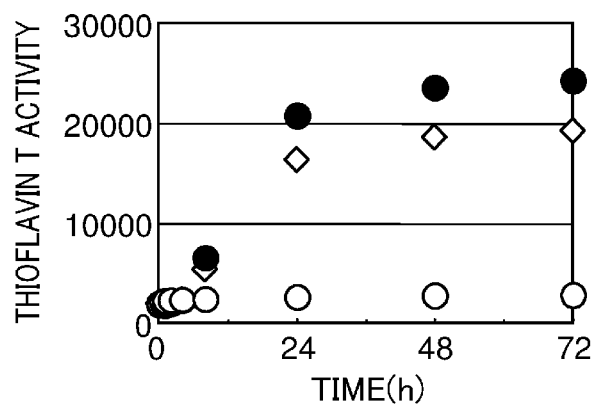
FIG. 6 shows the thioflavin T activity of 4-aminocatechol.
Figure 7:
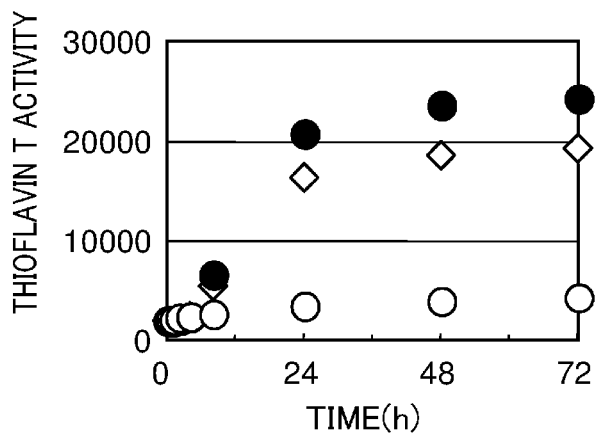
FIG. 7 shows the thioflavin T activity of 1,2,4-benzenetriol.
Figure 8A:
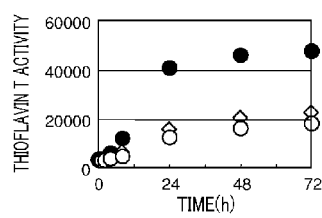
FIG. 8A shows that of catechol.
Figure 8B:
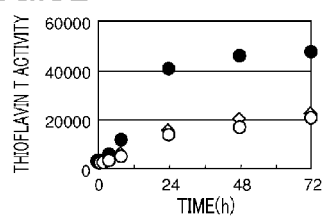
FIG. 8B shows that of 2,3-dihydroxybenzaldehyde.
Figure 8C:
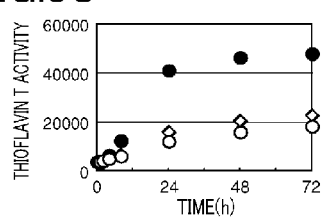
FIG. 8C shows that of 3-methoxycatechol.
Figure 8D:
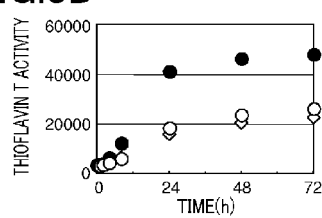
FIG. 8D shows that of 4-tert-butylcatechol.
Figure 8E:
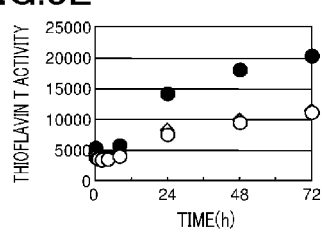
FIG. 8E shows that of 3,4-dihydroxybenzylamine.
Figure 8F:
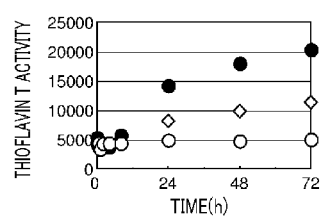
FIG. 8F shows that of 3-chloroacetylcatechol.
Figure 8G:
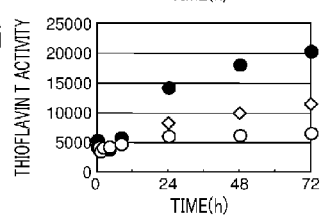
FIG. 8G shows that of 1-(3,4-dihydroxyphenyl)-2-morpholino ethanol.
Figure 8H:
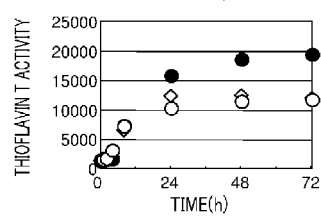
FIG. 8H shows that of pyrogallol.
Figure 8I:
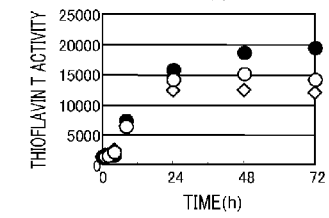
FIG. 8I shows that of 3,4-dihydroxyacetophenon.
Figure 8J:
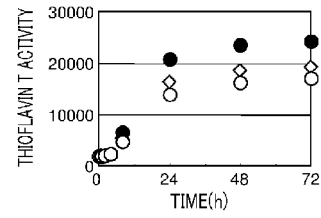
FIG. 8J shows that of 4-chlorocatechol.
Figure 8K:
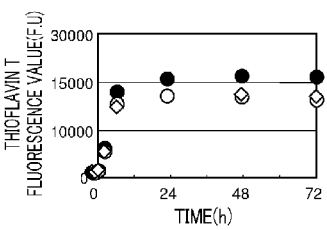
FIG. 8K shows that of 3-(3,4-dihydroxyphenyl)-3-hydroxy-2-(isopropylamino)propionate.

In vivo, most natural product derived catechol derivatives will have a side chain comprised of carbon chains at their position 4. Meanwhile, according to the present invention, a side chain comprised of elements other than carbon chains was newly studied. FIG. 6 shows the thioflavin T activity of 4-aminocatechol. FIG. 7 shows the thioflavin T activity of 1,2,4-benzenetriol. In FIGS. 6 and 7, the solid circles ● indicate the thioflavin T activity measured in the absence of any of these compounds, the open circles ○ indicate the thioflavin T activity measured in the presence of 1 µM of each compound, and the open diamonds ◇ indicate the thioflavin T activity measured under the same condition and in the presence of 1 µM of isoproterenol.

As shown in FIGS. 6 and 7, 4-aminocatechol (represented by the following Chemical Formula (27)) and 1,2,4-benzenetriol (represented by the following Chemical Formula (28)), which are compounds including an amino group and a hydroxyl group, inhibited the tau polymerization more strongly at a concentration of 1 µM than isoproterenol and catechol did. On the other hand, as shown in FIG. 5, no tau polymerization inhibitory activity was observed in 4-Nitropyrocatechol (represented by the following Chemical Formula (29)) in which a nitro group was substituted for the position 4.

Structural development was further carried out on 4-aminocatechol. As a result, as shown in FIG. 5, 4-aminophenol (represented by the following Chemical Formula (30)) and 3-aminophenol (represented by the following Chemical Formula (31)), from both of which one hydroxyl group had been removed, produced only diminished effects, and 3,4-(methylenedioxy)aniline (indicated by 3,4-MDA and represented by the following Chemical Formula (32)) had lost its tau polymerization inhibitory activity, in which two hydroxyl groups were replaced.

(27)
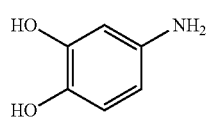

(28)
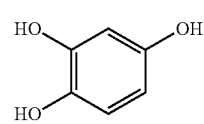

(29)
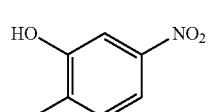

(30)
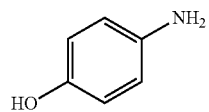

(31)
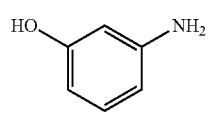

(32)
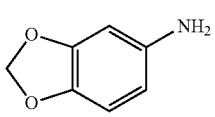

FIG. 8 shows the thioflavin T activities of various kinds of compounds, wherein: FIG. 8A shows that of catechol; FIG. 8B shows that of 2,3-dihydroxybenzaldehyde; FIG. 8C shows that of 3-methoxycatechol; FIG. 8D shows that of 4-tert-butylcatechol; FIG. 8E shows that of 3,4-dihydroxybenzylamine; FIG. 8F shows that of 3-chloroacetylcatechol; FIG. 8G shows that of 1-(3,4-dihydroxyphenyl)-2-morpholinoethanol; FIG. 8H shows that of pyrogallol; FIG. 8I shows that of 3,4-dihydroxyacetophenon; FIG. 8J shows that of 4-chlorocatechol; and FIG. 8K shows that of 3-(3,4-dihydroxyphenyl)-3-hydroxy-2-(isopropylamino)propionate.

In FIG. 8, the solid circles ● indicate the thioflavin T activity measured in the absence of any of these compounds, the open circles ○ indicate the thioflavin T activity measured in the presence of 1 µM of each compound, and the open diamonds ◇ indicate the thioflavin T activity measured under the same condition and in the presence of 1 µM of isoproterenol. As shown in FIG. 8, these compounds turned out to have tau aggregation inhibitory activity. Also, as shown in FIGS. 6 and 7 referred to above, the present inventors discovered that compounds including an amino group and a hydroxyl group at position 4 of the catechol nucleus functioning as a tau polymerization inhibitor inhibited the tau polymerization strongly.

Figure 9:
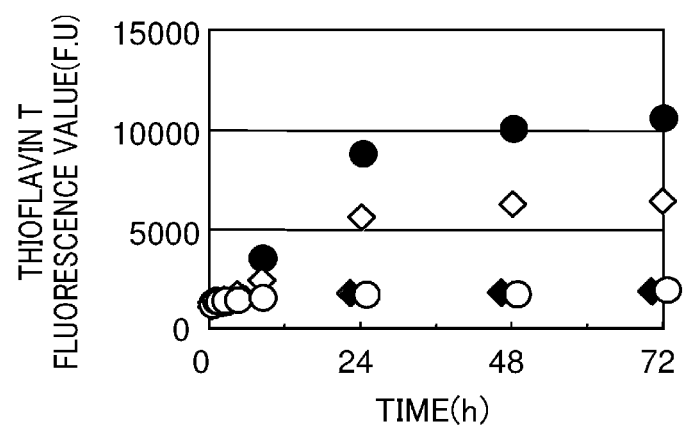
FIG. 9 shows the thioflavin T activity of aminocatechol.

A site-by-site difference caused by amino substitution for the catechol nucleus was further examined. FIG. 9 shows the thioflavin T activity of 3-aminocatechol (represented by the following Chemical Formula (33)).

(33)
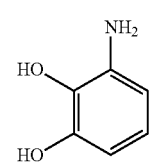

In FIG. 9, the solid circles ● indicate the thioflavin T activity measured in the absence of any of these compounds, the open circles ○ indicate the thioflavin T activity measured in the presence of 1 μM of 3-aminocatechol, the open diamonds ◇ indicate the thioflavin T activity measured under the same condition and in the presence of 1 μM of isoproterenol, and the solid diamonds ◆ indicate the thioflavin T activity measured under the same condition and in the presence of 1 μM of 4-aminocatechol. The present inventors discovered that such a compound including an amino group at position 3 of the catechol nucleus inhibited the tau polymerization as strongly as 4-aminocatechol did.

Next, the present inventors studied the influence to be caused by adding a side chain to the amino group in 4-aminocatechol. The compounds examined were 4-(isopentylamino) catechol (represented by the following Chemical Formula (34)), 4-(morpholinocarbonylamino) catechol (represented by the following Chemical Formula (35)), 4-(4-aminobutanoylamino) catechol (represented by the following Chemical Formula (36)), and 4-(diisopentylamino) catechol (represented by the following Chemical Formula (37)).

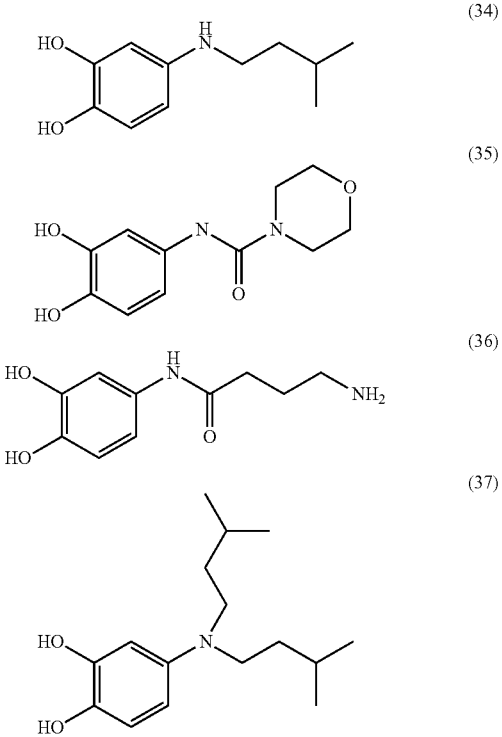

FIG. 10 shows the thioflavin T activities of various kinds of compounds, wherein: FIG. 10A shows that of 4-(isopentylamino) catechol; FIG. 10B shows that of N-(3,4-dihydroxyphenyl)morpholine-4-carboxyamide; FIG. 10C shows that of 4-(4-aminobutanoylamino) catechol; and FIG. 10D shows that of 4-(diisopentylamino) catechol. In FIG. 10, the solid circles ● indicate the thioflavin T activity measured in the absence of any of these compounds, the open circles ○ indicate the thioflavin T activity measured in the presence of 1 μM of each of these compounds, the open diamonds ◇ indicate the thioflavin T activity measured under the same condition and in the presence of 1 μM of isoproterenol, and the solid diamonds ◇ indicate the thioflavin T activity measured under the same condition and in the presence of 1 μM of 4-aminocatechol.

Figure 10A:
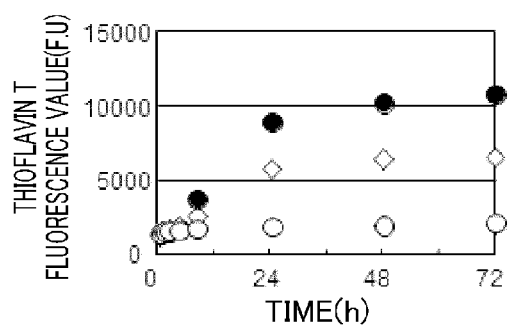
FIG. 10A shows that of 4-(isopentylamino) catechol.
Figure 10B:
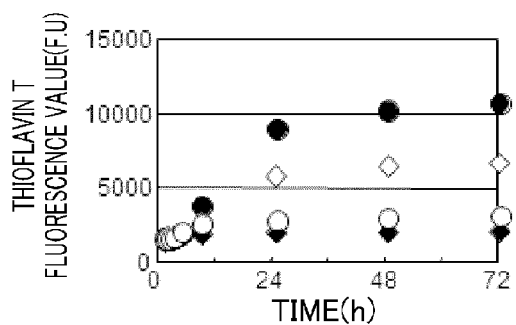
FIG. 10B shows that of 4-(morpholino carbonylamino) catechol.
Figure 10C:
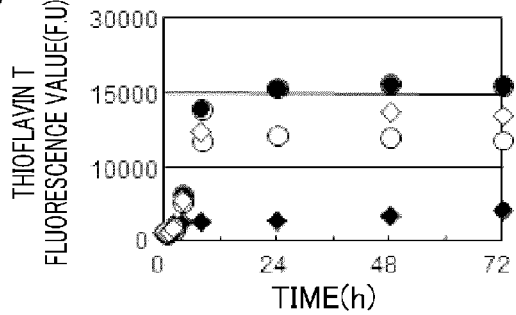
FIG. 10C shows that of 4-(4-aminobutanoylamino) catechol.
Figure 10D:
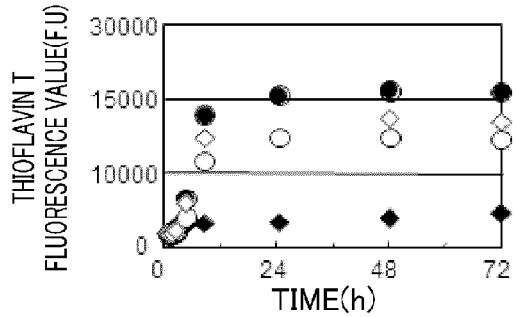
FIG. 10D shows that of 4-(diisopentylamino) catechol.

As shown in FIG. 10A, even if the 4-amino group was partially replaced with isopentyl, 4-aminocatechol's intense tau polymerization inhibitory activity did not change. On the other hand, as shown in FIG. 10B, if the 4-amino group was partially replaced with morpholine 4-carboxyamide, 4-aminocatechol's intense tau polymerization inhibitory activity slightly decreased. In contrast, as shown in FIGS. 10C and 10D, if the 4-amino group was partially replaced with 4-aminobutaneamide and diisopentyl, respectively, 4-aminocatechol's intense tau polymerization inhibitory activity decreased significantly to almost the same level as isoproterenol's. Thus, the present inventors discovered that as for 4-aminocatechol, in particular, a mono alkylated derivative of the amino group at position 4 had significant tau aggregation inhibitory effect. Meanwhile, the present inventors also discovered that addition of an electron-withdrawing side chain to the amino group at position 4 and dialkylation thereof affected the tau aggregation inhibitory effect.

Figure 11:
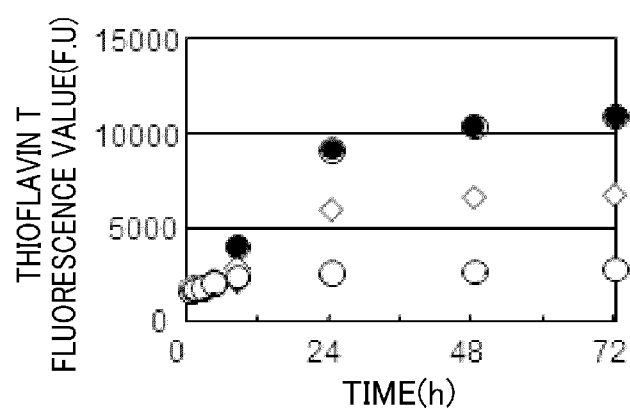
FIG. 11 shows the thioflavin T activity of 4-methoxycatechol.
Figure 12A:
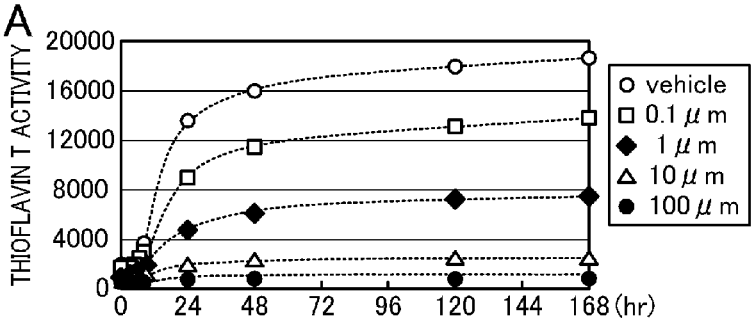
FIG. 12A shows that of methylene blue.
Figure 12B:
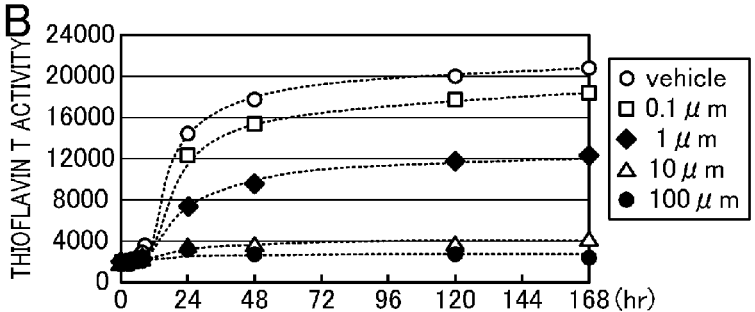
FIG. 12B shows that of isoproterenol.
Figure 12C:
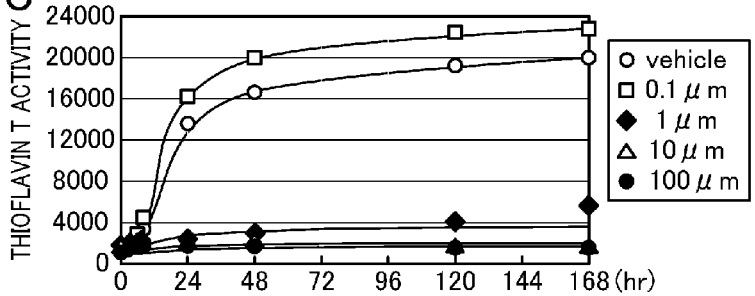
FIG. 12C shows that of 4-aminocatechol.
Figure 12D:
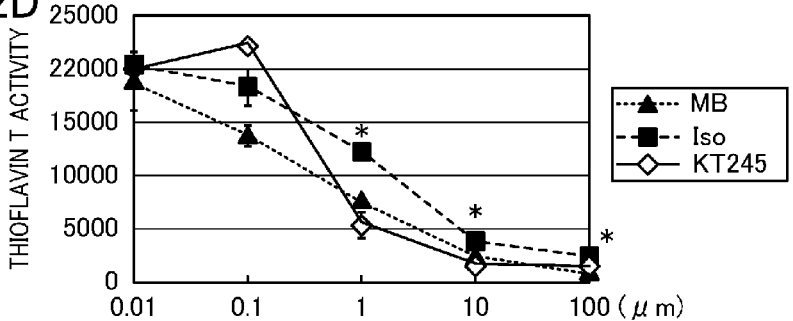
FIG. 12D shows, in comparison, those of methylene blue, isoproterenol and 4-aminocatechol.

Next, the present inventors studied the influence to be caused by adding a side chain to the hydroxyl group at position 4 of 1,2,4-benzenetriol. FIG. 11 shows the thioflavin T activity of 4-methoxycatechol (represented by the following Chemical Formula (38)) in which the hydroxyl group at position 4 of 1,2,4-benzenetriol was replaced with a methoxyl group.

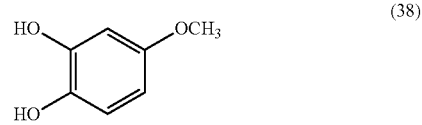

In FIG. 11, the solid circles ● indicate the thioflavin T activity measured in the absence of any compound, the open circles ○ indicate the thioflavin T activity measured in the presence of 1 of 4-methoxycatechol, the open diamonds ◇ indicate the thioflavin T activity measured under the same condition and in the presence of 1 μM of isoproterenol, and the solid diamonds ◇ indicate the thioflavin T activity measured under the same condition and in the presence of 1 μM of 4-aminocatechol. As shown in FIG. 11, alkylation of the hydroxyl group at position 4 of 1,2,4-benzenetriol did not affect 1,2,4-benzenetriol's intense tau polymerization inhibitory activity.

Furthermore, 4-aminocatechol was further compared to methylene blue and isoproterenol, which are compounds that are known to have tau polymerization inhibitory activity.

FIG. 12 shows the thioflavin T activities of various kinds of compounds, wherein: FIG. 12A shows that of methylene blue; FIG. 12B shows that of isoproterenol; FIG. 12C shows that of 4-aminocatechol; and FIG. 12D shows, in comparison, those of methylene blue, isoproterenol and 4-aminocatechol. These compounds were prepared to have concentrations of 0.1, 1, 10 and 100 μM, respectively, to examine their tau polymerization inhibitory activity. As shown in FIG. 12, when the thioflavin T activity was used as an index, inhibition of the activity was indicated more significantly than isoproterenol at every concentration equal to or greater than 1 μM. In this case, methylene blue was considered a reference, because methylene blue is a highly colored compound.

Figure 13A:
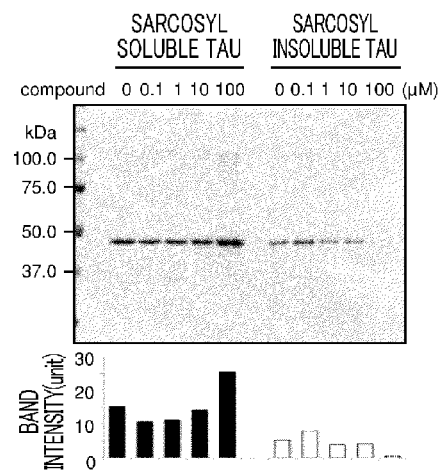
FIGS. 13A, 13B and 13C show the results of electrophoresis carried out on methylene blue, isoproterenol, and 4-aminocatechol, respectively.
Figure 13B:
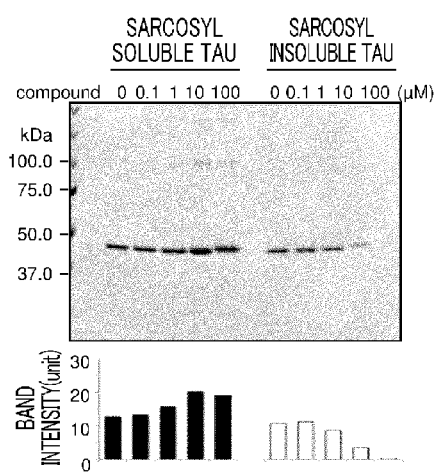
Figure 13C:
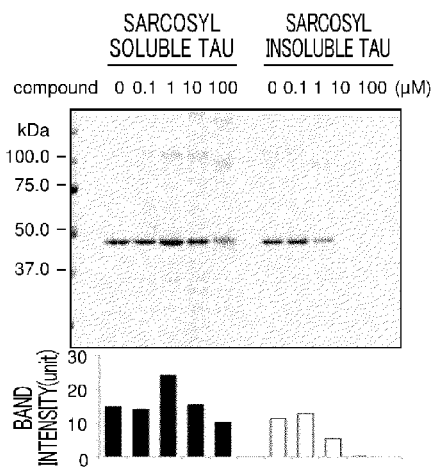

Next, samples that had been subjected to incubation for 168 hours were recovered to measure the quantity of sarcosyl insoluble tau. FIG. 13 shows the results of electrophoresis carried out on sarcosyl soluble tau and sarcosyl insoluble tau, wherein FIGS. 13A, 13B and 13C show the results of electrophoresis carried out on methylene blue, isoproterenol, and 4-aminocatechol, respectively. As shown in FIG. 13, each drug inhibited the tau polymerization depending on the concentration. Specifically, at as low a concentration as 1 μM, 4-aminocatechol reduced sarcosyl insoluble tau polymers more significantly than methylene blue and isoproterenol did.

Figure 14A:
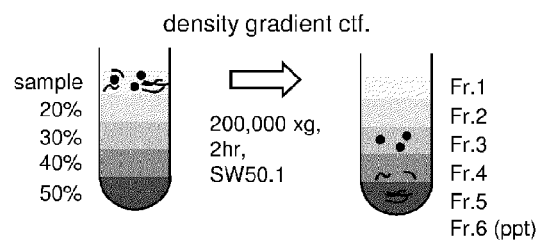
FIG. 14A illustrates how the polymerized tau's densities were fractionated by sucrose density-gradient centrifugation.

Next, to examine the tau polymerization inhibition mechanism, polymerized tau's densities were fractionated by sucrose density-gradient centrifugation. As shown in FIG. 14A, most of the soluble tau is recovered in Fraction 1 and only a part of the tau is recovered in Fraction 2. However, it is known that due to polymerization through heparin, fibrosed tau is recovered in Fractions 4 and 5 and oligomer tau is recovered in Fraction 3.

Figure 14B:
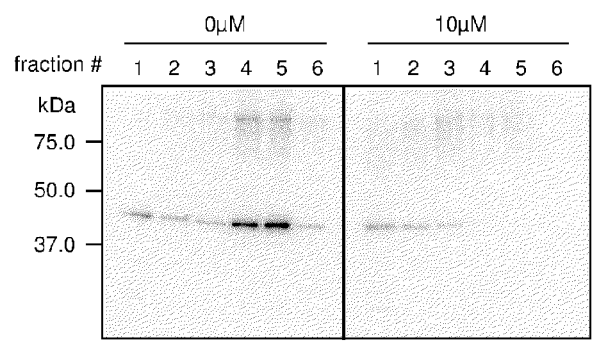
FIGS. 14B, 14C and 14D show the results of electrophoresis carried out on methylene blue, isoproterenol, and 4-aminocatechol, respectively.
Figure 14C:
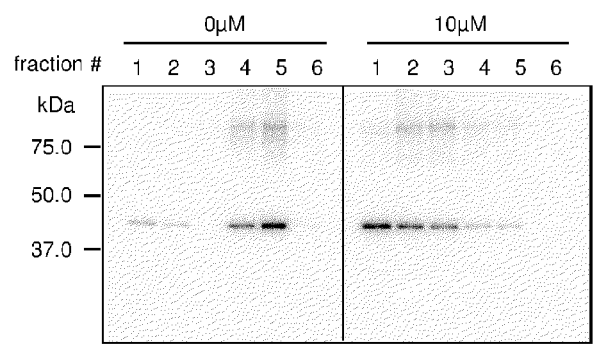
Figure 14D:
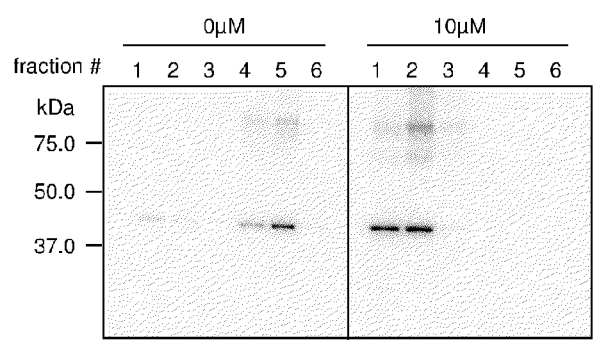

FIGS. 14B, 14C and 14D show the results of electrophoresis carried out on methylene blue, isoproterenol, and 4-aminocatechol, respectively. As shown in FIGS. 14B to 14D, in the presence of 10 μM of methylene blue or isoproterenol, the quantity of the tau recovered in Fractions 4 and 5, which would contribute to forming tau fibers, was seen to decrease significantly, and the quantity of the tau recovered in Fraction 3, corresponding to oligomer tau, was also seen to decrease. On the other hand, in the presence of 10 μM of 4-aminocatechol, both the fibrosed tau and the oligomer tau were eliminated almost completely. Thus, the present inventors discovered that 4-aminocatechol reduced the polymerization of tau and formation of oligomer at a lower concentration than an existent tau polymerization inhibitor.

The results of these experiments revealed that a compound including: catechol; and a 4-substituted catechol structure compound having, at position 4 of its catechol ring, an electron-donating substituent R other than a hydrocarbon group; or a 3-substituted catechol structure compound having, at position 3 of its catechol ring, an electron-donating substituent R; or a salt of any of these compounds has a catechol nucleus with intense tau polymerization inhibitory activity. Comparing its tau polymerization inhibitory activity to those of isoproterenol and catechol, it can be seen that the activity would be enhanced significantly (e.g., approximately five to tenfold) by adding an electron-donating side chain such as 4-aminocatechol. By either being used as it is or going through an appropriate structural development, the compound such as 4-aminocatechol or 1,2,4-benzenetriol obtained by the present invention may turn into a tau polymerization inhibitor exhibiting effectiveness at lower concentrations than previous compounds, and therefore, can be a far more effective dementia remedy for treating Alzheimer's disease and all the other kinds of tauopathies. Particularly, considering the facts that dementia patients are the elderly, long-term administration is expected, the drug needs to be absorbed into the patient's body and transferred into his or her brain, a certain in-brain concentration needs to be maintained for a long time, and it is difficult for the dementia patients to comply with the medication schedule exactly, it can be said that such a compound exhibiting high effectiveness at lower concentrations is advantageous. In addition, such a compound according to the present invention, of which the basic skeleton is 4-aminocatechol or 1,2,4-benzenetriol, would be used as not only an effective dementia remedy but also an effective tau research tool as well.

INDUSTRIAL APPLICABILITY

The present invention is useful for treating tauopathies.

What is claimed is:
1. A method of alleviating occurrence of and/or treating a tauopathy in a subject, the method comprising:
    administering an effective dose of a tau aggregation inhibitor to the subject in need of such alleviation and/or treatment,
    wherein the tau aggregation inhibitor comprises:
    a 4-substituted catechol structure compound having, at position 4 of its catechol ring, substituent R which is any one of an amino group, a hydroxyl group, an alkoxy group and a thiol group; or
    a 3-substituted catechol structure compound having, at position 3 of its catechol ring, substituent R which is any one of an amino group, an alkoxy group or a thiol group; or
    a salt of any of these compounds.
2. The method according to claim 1, wherein the tauopathy is AD, Down's syndrome, frontotemporal dementia, cotricobasal degeneration (CBD) or progressive supranuclear palsy (PSP).

* * * * *

UNITED STATES PATENT AND TRADEMARK OFFICE
CERTIFICATE OF CORRECTION

PATENT NO. : 9,907,799 B2
APPLICATION NO. : 14/781897
DATED : March 6, 2018
INVENTOR(S) : Tomohiro Miyasaka et al.

It is certified that error appears in the above-identified patent and that said Letters Patent is hereby corrected as shown below:

On the Title Page

Item (57), (Abstract) at Line 10, Change "cotricobasal" to --corticobasal--.

In the Drawings

Sheet 2 of 10 (X-axis, FIG. 5) at Line 1 (approx.), Change "Benzentriol" to --Benzenetriol--.

In the Specification

In Column 1 at Line 65, Change "naptho quinone" to --napthoquinone--.

In Column 2 at Line 67, Change "dihydroxyacetophenon;" to --dihydroxyacetophenone;--.

In Column 4 at Line 58, Change "3-pyrrazolyl" to --3-pyrazolyl--.

In Column 4 at Line 59, Change "2-pyrridyl" to --2-pyridyl--.

In Column 4 at Line 59, Change "3-pyrridyl" to --3-pyridyl--.

In Column 4 at Line 59, Change "4-pyrridyl" to --4-pyridyl--.

In Column 6 at Line 44, Change "cotricobasal" to --corticobasal--.

In Column 8 at Line 35 (approx.), Change "(infinit" to --(infinite--.

In Column 9 at Line 66, Change "homoveratylamine" to --homoveratrylamine--.

In Column 11 at Line 43, Change "FIG." to --FIGS.--.

Signed and Sealed this
Twenty-eighth Day of May, 2019

Andrei Iancu
*Director of the United States Patent and Trademark Office*

CERTIFICATE OF CORRECTION (continued)
U.S. Pat. No. 9,907,799 B2

In Column 14 at Line 35, Change "dihydroxyacetophenon;" to --dihydroxyacetophenone;--.

In Column 16 at Line 7, Change "4-aminobutaneamide" to --4-aminobutanamide--.

In the Claims

In Column 18 at Lines 43 (approx.), In Claim 2, change "cotricobasal" to --corticobasal--.